United States Patent
Melamed

(10) Patent No.: US 10,780,135 B2
(45) Date of Patent: Sep. 22, 2020

(54) PROBIOTIC FORMULATION AND METHOD FOR WEIGHT LOSS TREATMENT

(71) Applicant: Hooman M. Melamed, Marina del Rey, CA (US)

(72) Inventor: Hooman M. Melamed, Marina del Rey, CA (US)

(*) Notice: Subject to any disclaimer, the term of this patent is extended or adjusted under 35 U.S.C. 154(b) by 85 days.

(21) Appl. No.: 15/946,581

(22) Filed: Apr. 5, 2018

(65) Prior Publication Data

US 2019/0307816 A1    Oct. 10, 2019

(51) Int. Cl.

| | |
|---|---|
| *A61K 35/747* | (2015.01) |
| *A61K 9/48* | (2006.01) |
| *A23L 33/135* | (2016.01) |
| *A61K 31/733* | (2006.01) |
| *A61K 9/20* | (2006.01) |
| *A23L 33/00* | (2016.01) |
| *A61P 3/04* | (2006.01) |

(52) U.S. Cl.
CPC .......... *A61K 35/747* (2013.01); *A23L 33/135* (2016.08); *A23L 33/30* (2016.08); *A61K 9/205* (2013.01); *A61K 9/4866* (2013.01); *A61P 3/04* (2018.01); *A23V 2002/00* (2013.01)

(58) Field of Classification Search
CPC .... A61K 35/747; A61K 9/4866; A61K 9/205; A61K 31/733; A61K 9/0095; A61K 9/0053; A23L 33/135; A23L 33/30; A61P 3/04; A23V 2002/00
See application file for complete search history.

(56) References Cited

U.S. PATENT DOCUMENTS

2014/0079676 A1*   3/2014   Olmstead ............. A61K 9/0053
424/93.45

OTHER PUBLICATIONS

Niness. Inulin and Oligofructose: What Are They? J. Nutr. 129: 1402S-1406S (Year: 1999).*
Keybiotics. downloaded from web.archive.org/web/20131130095953/ https://wholebodyresearch.com/p/ordernow2.php. p. 1-3 (Year: 2013).*

* cited by examiner

*Primary Examiner* — Taeyoon Kim
(74) *Attorney, Agent, or Firm* — Omni Legal Group; Omid E. Khalifeh; Lora A. Petersen

(57) ABSTRACT

A composition of probiotics is provided which promotes weight loss and maintenance thereof. More particularly, a probiotic mixture of *Lactobacillus gasseri*, *Lactobacillus fermentum*, and *Lactobacillus rhamnosus* are provided to reduce body adiposity, decrease inflammation of adipose tissue, and enhance metabolism in optional combination with prebiotics and excipients such as flow agents and binders. A method of administering the probiotic composition to an individual user is also provided.

10 Claims, No Drawings

PROBIOTIC FORMULATION AND METHOD FOR WEIGHT LOSS TREATMENT

GOVERNMENT CONTRACT

Not applicable.

CROSS-REFERENCE TO RELATED APPLICATIONS

Not applicable.

STATEMENT RE. FEDERALLY SPONSORED RESEARCH/DEVELOPMENT

Not applicable.

COPYRIGHT & TRADEMARK NOTICES

A portion of the disclosure of this patent document may contain material, which is subject to copyright protection. This patent document may show and/or describe matter, which is or may become trade dress of the owner. The copyright and trade dress owner has no objection to the facsimile reproduction by any one of the patent document or the patent disclosure, as it appears in the Patent and Trademark Office patent files or records, but otherwise reserves all copyrights and trade dress rights whatsoever.

TECHNICAL FIELD

The disclosed subject matter relates generally to a composition of probiotics; and more particularly, to a probiotic formulation effective in achieving and maintaining weight loss.

BACKGROUND

The prevalence of obesity is increasing in virtually all developed nations. Obesity, in turn, amplifies the risk of further chronic diseases including type 2 diabetes, cardiovascular disease, coronary artery disease, hypertension, stroke, hypercholesterolemia, cholelithiasis, fatty liver disease, musculoskeletal disorders (including back and joint problems), obstructive sleep apnea, and certain cancers. Many afflicted individuals also experience social consequences and isolation.

Obesity is associated with an imbalance between energy intake and expenditure. The gut microflora has been suggested to be environmental factor that regulates this energy balance in humans. Moreover, metabolism and by extension, body weight, are further influenced by the inflammatory response and impaired gut hormone signaling affecting energy expenditure. Indeed, inflammation is closely related to hypertrophy of adipose tissue. The composition of gut microbiota is understood to play a role in the regulation of the inflammatory response and hormone signaling.

A number of surgical options exist to treat obesity. For instance, gastric bypass involves limiting the portion of the stomach that holds food. Similarly, laparoscopic gastric banding requires a band containing an inflatable balloon be fixed in place around the upper part of the stomach. These options are invasive, expensive, and can lead to further health complications. Moreover, these types of medical intervention are often only available to those who suffer from severe obesity. The food industry has also responded to the obesity problem by developing products with low energy density, that is, low fat and low carbohydrate concentrations.

Probiotic formulations have emerged as an alternative treatment for a number of diseases. Probiotics are live microorganisms that confer a health benefit upon administration of an adequate dose. These products function by recolonizing the intestinal microflora and thereafter stabilizing and maintaining a desirable community of microorganisms. Indeed, many probiotic products are aimed at delivering beneficial bacterial cells to the intestinal tract. However, not all probiotics have the same effect and each probiotic treatment is limited in application and effectiveness.

Although various solutions have been proposed, none combine the characteristics of the present invention. Thus, there is a need for a probiotic formulation which would assist in regulating the energy balance in humans and as a result, lead to anti-obesity effects.

SUMMARY OF THE INVENTION

The present disclosure is directed to a probiotic composition for weight loss comprising a mixture of *Lactobacillus gasseri*, *Lactobacillus fermentum*, and *Lactobacillus rhamnosus*. In a preferred embodiment, these three bacterial strains are present in equal proportions.

For purposes of summarizing, certain aspects, advantages, and novel features have been described. It is to be understood that not all such advantages may be achieved in accordance with any one particular embodiment. Thus, the disclosed subject matter may be embodied or carried out in a manner that achieves or optimizes one advantage or group of advantages without achieving all advantages as may be taught or suggested.

It is a primary object of this disclosure to provide a probiotic formulation, which promotes the reduction of body weight and maintenance of weight loss through recolonization of the intestinal flora with beneficial bacteria.

In accordance with one embodiment, the composition may comprise between about 25 to 35 weight percent *Lactobacillus gasseri*, between about 25 to 35 weight percent *Lactobacillus fermentum*, and between about 25 to 35 weight percent *Lactobacillus rhamnosus*.

In an embodiment, the composition may be placed into capsules or tablets for oral administration. In such an embodiment the composition may further comprise a flow agent to facilitate the manufacturing process of such capsule or tablet and smooth the digestive process thereof.

In yet another embodiment, the composition further comprises a prebiotic as a food source to the beneficial bacteria while simultaneously resisting degradation by the intestinal tract. It is further envisioned that the composition may comprise live strains of probiotics. In one embodiment, the probiotics composition may be comprised of non-genetically modified organisms.

In some embodiments, the method may comprise the steps of administering a therapeutically effective amount of the mixture of beneficial probiotic microflora and a pharmaceutically acceptable carrier.

One or more of the above-disclosed embodiments, in addition to certain alternatives, are provided in further detail below. The disclosed subject matter is not, however, limited to any particular embodiment disclosed.

Advantages

Several advantages of one or more aspects are to provide a probiotic formulation that:

(a) facilitates weight loss;
(b) assists in maintenance of healthy body weight;
(c) inhibits the inflammatory response of adipose tissue;
(d) supplants additional beneficial bacterial flora in the intestinal tract;
(e) suppress appetite;
(f) increase energy;
(g) increases mental clarity and focus; and
(h) improves overall digestive health.

These and other advantages of one or more aspects will become apparent from consideration of the ensuing description and accompanying examples. Although the description above contains many specifics, these should not be construed as limiting the scope of the embodiments but as merely providing illustrations of some of several embodiments. Thus, the scope of the embodiments should be determined by the claims that the appended and their legal equivalents, rather than by the examples given.

The description of the invention which follows, together with the accompanying examples should not be construed as limiting the invention to the examples shown and described, because those skilled in the art to which this invention pertains will be able to devise other forms thereof within the ambit of the appended claims.

DETAILED DESCRIPTION

Illustrated embodiments of the invention are described below. The showings are for purposes of illustrating preferred embodiments and not for purposes of limiting the same. The following explanation provides specific details for a thorough understanding of an enabling description for these embodiments. One skilled in the art will understand that the invention may be practiced without such details. In other instances, well-known structures and functions have not been shown or described in detail to avoid unnecessarily obscuring the description of the embodiments.

In an embodiment, the probiotic formulation includes beneficial bacteria, which have the characteristics of decreasing body weight, boosting the body's immune response, and enhancing the metabolism, causing less fat to be absorbed. A preferred embodiment of the formulation comprises a total of 37.5 billion colony-forming units (CFU) of beneficial bacteria. In other embodiments, the formulation may comprise between about 5 billion to 50 billion CFU.

The composition comprises *Lactobacillus gasseri*, *Lactobacillus fermentum*, and *Lactobacillus rhamnosus*. In some embodiments, the composition may comprise between about 10 to 50 weight percent *Lactobacillus gasseri*, between about 10 to 50 weight percent *Lactobacillus fermentum*, and between about 10 to 50 weight percent *Lactobacillus rhamnosus*. Preferably, the composition may comprise between about 25 to 35 weight percent *Lactobacillus gasseri*, between about 25 to 35 weight percent *Lactobacillus fermentum*, and between about 25 to 35 weight percent *Lactobacillus rhamnosus*. One of ordinary skill in the art will recognize the composition can contain varying amounts of the beneficial bacteria.

In some embodiments, *Lactobacillus gasseri* exhibits abdominal adiposity regulating properties, reduces visceral and subcutaneous fat, and generally exerts anti-obesity effects. In addition, the *Lactobacillus gasseri* inhibits pro-inflammatory gene expression in adipose tissue leading to reduction in visceral adipose tissue mass. In an embodiment, the *Lactobacillus fermentum* possesses cholesterol-lowering properties and creates an environment favoring fat oxidation over fat storage, ultimately leading to reduction in body adiposity. In some embodiments, the *Lactobacillus rhamnosus* may further accentuate body weight loss and helps maintain healthy body weight. The *Lactobacillus rhamnosus* is further characterized by its ability to support other bacterial species, enhancing the overall formulation of beneficial bacteria. In other embodiments, the *Lactobacillus fermentum* and *Lactobacillus rhamnosus* may also improve neurological and cognitive function.

The aforementioned probiotic formulation may be mixed together by conventional methods and placed into a pharmaceutically acceptable carrier. In an embodiment, the carrier may be a capsule for oral administration. In such an embodiment, an outer housing of the capsule is optionally made of gelatin or cellulose. Cellulose has the benefit of maintaining the formulation in intestinal fluid, disallowing premature breakdown in the upper gastrointestinal tract, so the product can reach the desired destination. Alternatively, the ingredients may be combined and formed into a tablet. In tablet form, cellulose may also be present to act as a binder to hold the tablet together.

The inventive composition may also be manifested in liquid or powder form. Moreover, a food product, such as yogurt or a dairy beverage, can act as the carrier to transport the beneficial bacteria into the digestive system. Indeed, yogurt and other dairy sources have proven to be ideal carriers for probiotics due to their ability to prevent degradation of the bacteria in the gut thereby facilitating colonization. Such foods products can be in solid or liquid/drinkable form. Further, the food product can contain all customary additives, including but not limited to, proteins, vitamins, minerals, trace elements, and other nutritional ingredients.

In certain embodiments, the composition may further comprise one or more prebiotics. Prebiotics resist breakdown in the gastrointestinal tract and increase probiotic functionality by acting as a food source for naturally occurring and added beneficial bacteria. Prebiotics promote the growth and proliferation of beneficial bacteria in the digestive system. In such embodiments where one or more prebiotics is present, such prebiotics are present in a quantity between about 10 to 50 percent weight. Preferably, the concentration of prebiotics ranges from about 15 to 25 weight percent.

In a preferred embodiment, the prebiotic is inulin. Inulin has also been found to independently facilitate weight loss by decreasing hunger and increasing satiety. In other embodiments, the prebiotic can be oligofructose, fructooligosaccharides, transgalactooligosaccharides, other non-digestible oligosaccharides, or pectin.

In an embodiment where the probiotic formulation is delivered as a capsule or tablet, the composition may further comprise one or more excipients to facilitate the manufacturing process by preventing the ingredients from adhering to machines. Moreover, such excipients render the capsule or tablet form easier to swallow and digest through the intestinal tract. The excipients may be a vegetable stearate, magnesium stearate, steric acid, ascorbyl palmitate, retinyl palmitate, or hyproxypropyl methylcellulose. In a preferred embodiment, the excipients are present in an amount between about 0 to 50 weight percent.

An example method for weight loss treatment with the probiotic formulation may comprise the steps of administering a therapeutically effective amount of the mixture of beneficial probiotic microflora and a pharmaceutically acceptable carrier. In certain embodiments, the therapeutically effective amount is between about 10 billion to 50 billion colony forming units (CFU) of the mixture of *Lac-* tobacillus gasseri, Lactobacillus fermentum, and Lactobacillus rhamnosus. Preferably, the therapeutically effective amount is 37.5 billion CFU.

EXAMPLES OF THE PREFERRED EMBODIMENT

In order to more fully teach what the Applicant regards as his invention, the following example is given. It should be understood that the formulations set forth in the Example is not to be construed as limiting of the scope of the invention, except so far as they yield a probiotic formulation having the desired properties and characteristics.

The following ingredients are an example of Applicant's invention with the percentages being given by weight of the probiotic formulation:

| Ingredient | Percentage |
| --- | --- |
| Lactobacillus gasseri | 25 |
| Lactobacillus fermentum | 25 |
| Lactobacillus rhamnosus | 25 |
| Prebiotics | 15 |
| Excipients | 10 |

CONCLUSIONS, RAMIFICATIONS, AND SCOPE

While certain embodiments of the invention have been illustrated and described, various modifications are contemplated and can be made without departing from the spirit and scope of the invention. For example, it is contemplated that various excipients may be included or substituted in the composition. In one contemplated embodiment, vegetable stearate may be an excipient. In other embodiments, other forms of steric acid may be used instead. Accordingly, it is intended that the invention not be limited, except as by the appended claim(s).

The teachings disclosed herein may be applied to other compositions, and may not necessarily be limited to any described herein. The elements and acts of the various embodiments described above can be combined to provide further embodiments. All of the above patents and applications and other references, including any that may be listed in accompanying filing papers, are incorporated herein by reference. Aspects of the invention can be modified, if necessary, to employ the compositions and concepts of the various references described above to provide yet further embodiments of the invention.

Particular terminology used when describing certain features or aspects of the invention should not be taken to imply that the terminology is being refined herein to be restricted to any specific characteristics, features, or aspects, of the ingredients with which that terminology is associated. In general, the terms used in the following claims should not be construed to limit the ingredients of the probiotic formulation disclosed in the specification unless the above description section explicitly defines such terms. Accordingly, the actual scope encompasses not only the disclosed embodiments, but also all equivalent ways of composing or implementing the disclosed ingredients. The above description of embodiments of the probiotic formulation is not intended to be exhaustive or limited to the precise form disclosed above or to a particular field of usage. While specific embodiments of, and examples for, the probiotic formulation and ingredients thereof are described above for illustrative purposes, various equivalent modifications are possible for which those skilled in the relevant art will recognize.

While certain aspects of the probiotic composition disclosed are presented below in particular claim forms, various aspects of the method and system are contemplated in any number of claim forms. Thus, the inventor reserves the right to add additional claims after filing the application to pursue such additional claim forms for other aspects of the probiotic formulation.

What is claimed is:

1. A probiotic formulation, comprising:
   a mixture of beneficial probiotic microflora, consisting of Lactobacillus gasseri, Lactobacillus fermentum, and Lactobacillus rhamnosus; and
   a pharmaceutically acceptable carrier, wherein an outer housing of the carrier is formed of cellulose, the cellulose being configured to maintain the formulation in intestinal fluid.

2. The probiotic formulation of claim 1, wherein the mixture of beneficial probiotic microflora comprises from about 10 to 50 weight percent Lactobacillus gasseri, from about 10 to 50 weight percent Lactobacillus fermentum, and from about 10 to 50 weight percent Lactobacillus rhamnosus.

3. The probiotic formulation of claim 1, wherein the mixture of beneficial probiotic microflora comprises from about 30 to 35 weight percent Lactobacillus gasseri, from about 30 to 35 weight percent Lactobacillus fermentum, and from about 30 to 35 weight percent Lactobacillus rhamnosus.

4. The probiotic formulation of claim 1, wherein the mixture of beneficial probiotic microflora is about between 5 billion and 50 billion colony forming units (CFU).

5. The probiotic formulation of claim 1, wherein the mixture of beneficial probiotic microflora is 37.5 billion CFU.

6. The probiotic formulation of claim 1, wherein the pharmaceutically acceptable carrier is a capsule.

7. The probiotic formulation of claim 1, further comprising
   a prebiotic acting as a food source for the mixture of probiotics.

8. The probiotic formulation of claim 7, wherein the prebiotic includes inulin.

9. The probiotic formulation of claim 7, wherein the prebiotic includes oligofructose.

10. The probiotics formulation of claim 7, wherein the prebiotic includes a non-digestible oligosaccharide.

* * * * *